(12) United States Patent
Propp

(10) Patent No.: US 8,053,624 B2
(45) Date of Patent: *Nov. 8, 2011

(54) REINFORCED CLOSURE ANCHOR

(75) Inventor: Donald J. Propp, Dewitt, MI (US)

(73) Assignee: Centurion Medical Products Corporation, Howell, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/759,934

(22) Filed: Apr. 14, 2010

(65) Prior Publication Data

US 2010/0198162 A1    Aug. 5, 2010

Related U.S. Application Data

(63) Continuation of application No. 12/690,315, filed on Jan. 20, 2010, which is a continuation-in-part of application No. 12/558,634, filed on Sep. 14, 2009, which is a continuation of application No. 12/011,692, filed on Jan. 29, 2008, now Pat. No. 7,626,070.

(51) Int. Cl.
*A61C 13/00* (2006.01)
*A61D 1/00* (2006.01)
*A61M 5/32* (2006.01)

(52) U.S. Cl. ............................ 602/41; 606/213; 604/15

(58) Field of Classification Search .................... 604/15, 604/180, 179, 174; 128/DIG. 26, 133, 132; 606/213, 215, 139, 216, 228–232; 602/41–43, 602/45, 52–54, 57–58
See application file for complete search history.

(56) References Cited

U.S. PATENT DOCUMENTS

| 6,124,521 | A | 9/2000 | Roberts | |
|---|---|---|---|---|
| 7,025,749 | B2* | 4/2006 | Propp | 604/180 |
| 7,294,752 | B1* | 11/2007 | Propp | 602/58 |
| 7,626,070 | B2* | 12/2009 | Propp | 602/41 |
| 7,723,561 | B2* | 5/2010 | Propp | 602/58 |
| 2005/0131329 | A1 | 6/2005 | Beaudry | |
| 2005/0261623 | A1 | 11/2005 | Propp | |
| 2007/0060892 | A1 | 3/2007 | Propp | |
| 2008/0200880 | A1 | 8/2008 | Kyvik et al. | |
| 2010/0004680 | A1* | 1/2010 | Propp | 606/213 |
| 2010/0121282 | A1* | 5/2010 | Propp | 604/180 |
| 2010/0160866 | A1* | 6/2010 | Propp | 604/180 |

* cited by examiner

*Primary Examiner* — Patricia Bianco
*Assistant Examiner* — Tarla Patel
(74) *Attorney, Agent, or Firm* — Bill C. Panagos; Linda D. Kennedy; Rader, Fishman & Grauer PLLC

(57) ABSTRACT

A reinforced closure anchor includes a first layer having an adhesive side, an opposite non-adhesive side, and an outer edge. An anchor member layer having a reinforcing structure is disposed on the first layer. The anchor member includes an adhesive side and an opposite non-adhesive side. The anchor member adhesive side is adhered to the first layer non-adhesive side or the first layer adhesive side. The anchor member may be generally centered between ends of the first layer, the anchor member may extend to portions of the outer edge of the first layer, and the anchor member may have a shape that generally corresponds in shape to a middle portion of the first layer.

12 Claims, 9 Drawing Sheets

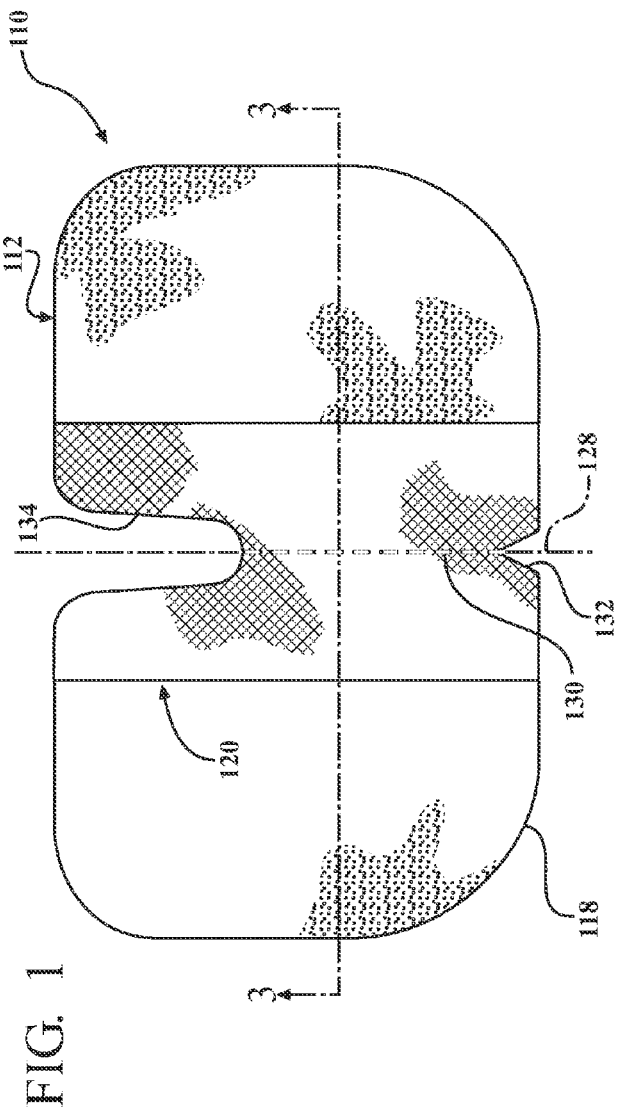
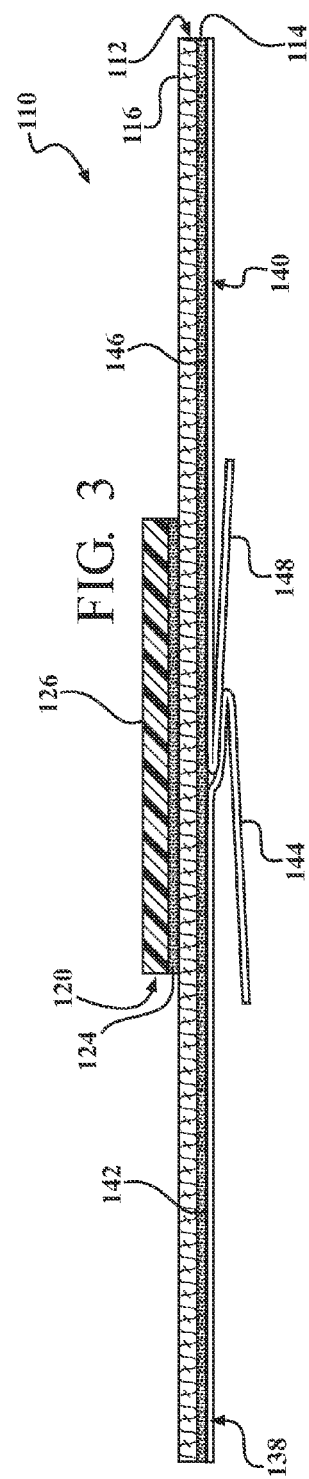

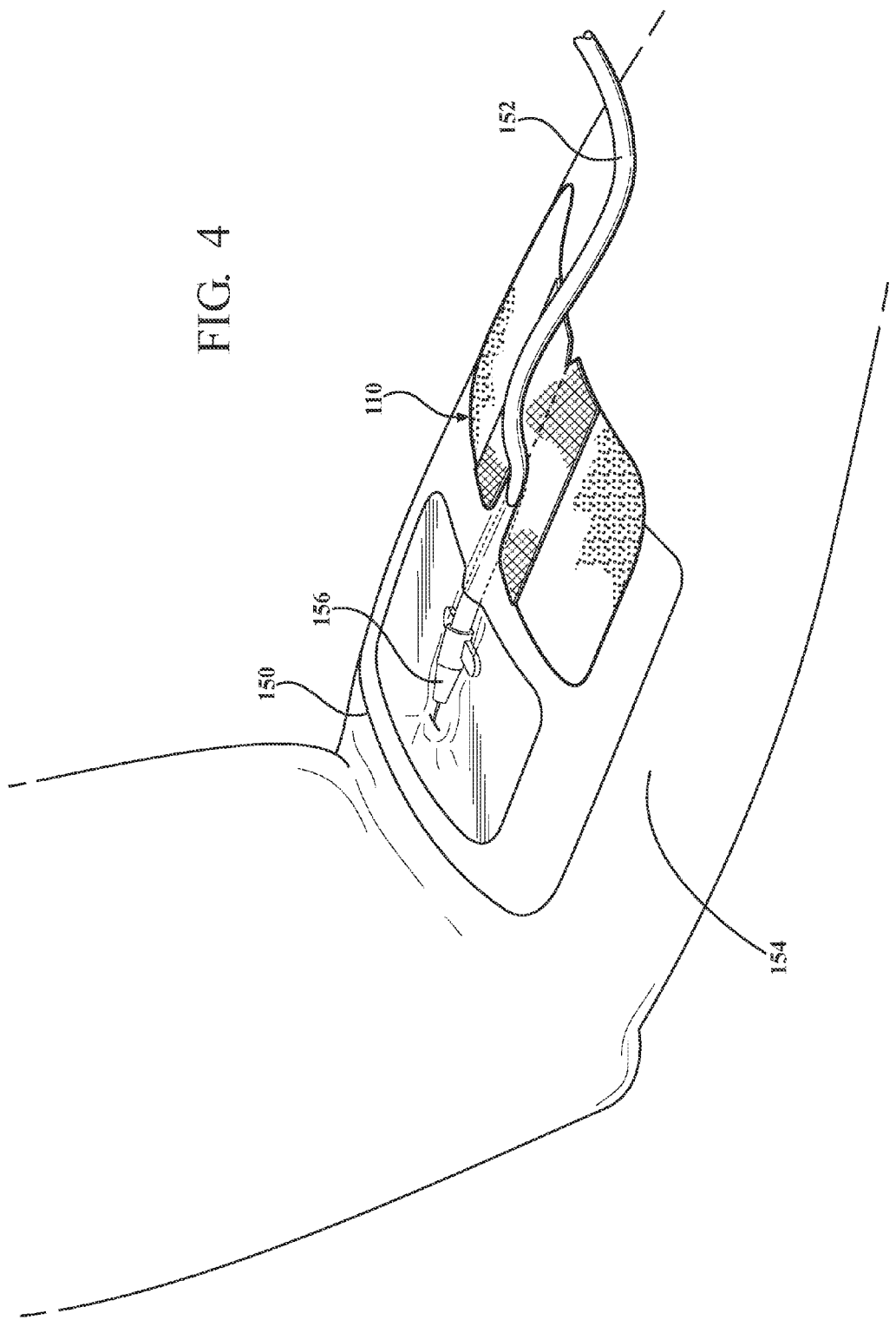

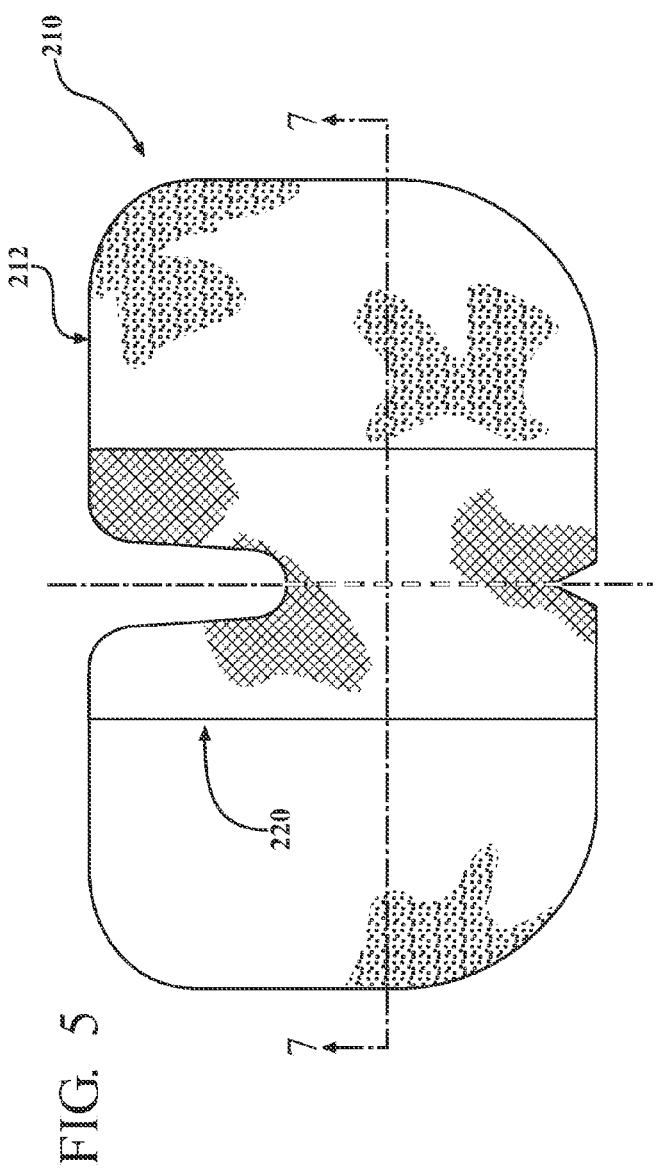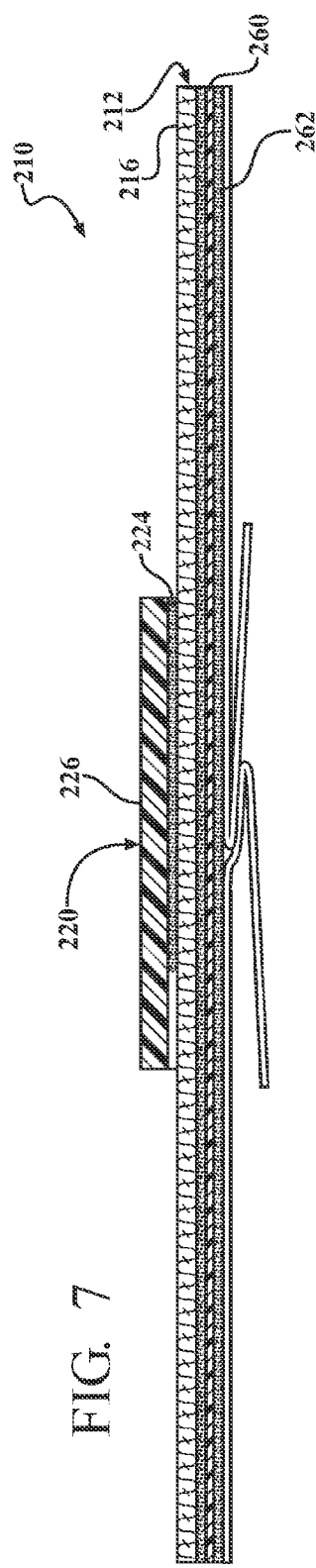

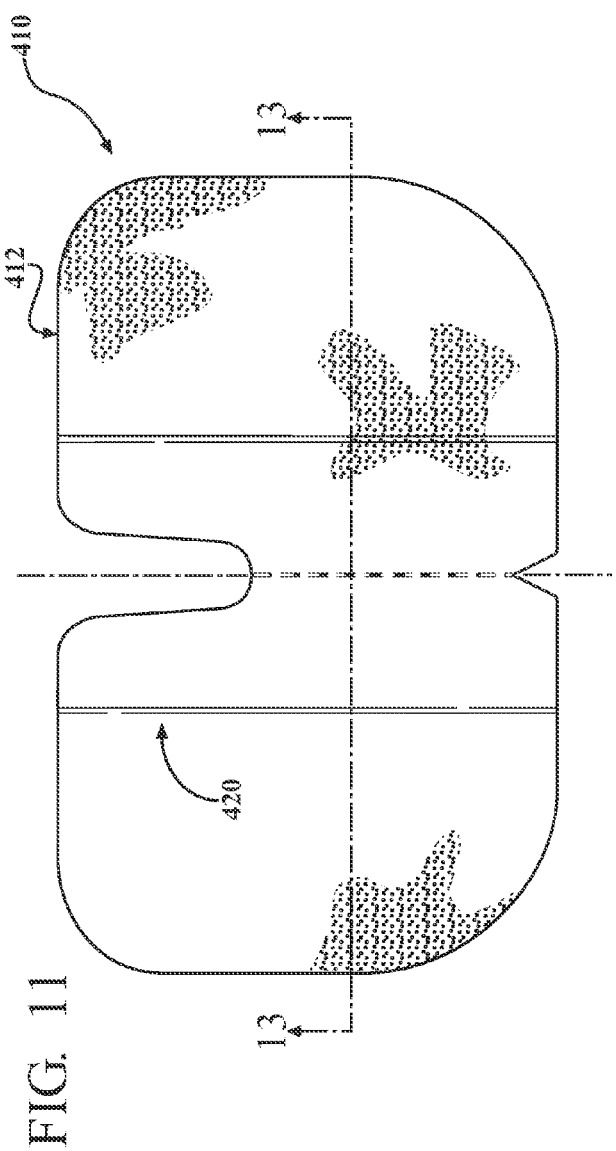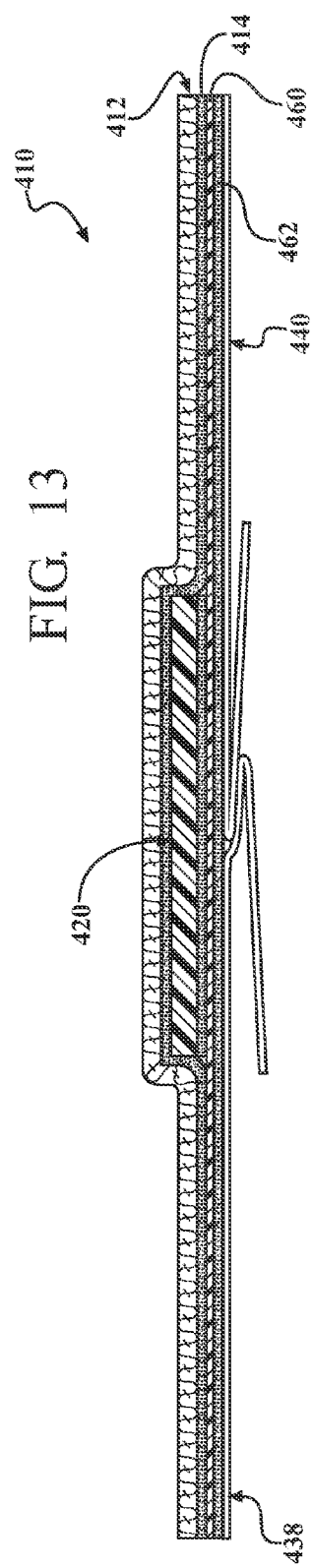

REINFORCED CLOSURE ANCHOR

CROSS REFERENCE TO RELATED APPLICATIONS

This application is a continuation of U.S. patent application Ser. No. 12/690,315, filed Jan. 20, 2010, which is a continuation-in-part of U.S. patent application Ser. No. 12/558,634, filed Sep. 14, 2009, which is a continuation of U.S. patent application Ser. No. 12/011,692, filed Jan. 29, 2008.

TECHNICAL FIELD

This invention relates to medical dressings, and more particularly to reinforced closure members for closing a portion of a medical dressing and anchoring medical tubing.

BACKGROUND OF THE INVENTION

It is known in the art relating to medical dressings for the protection and securement of catheters to apply a dressing to a patient's skin to cover a catheter insertion site at which the catheter punctures a patient's skin. It is also common for medical clinicians (i.e., doctors, nurses, and other medical personnel) to alternatively or additionally apply strips of medical grade tape to attempt to secure the catheter or associated medical tubing. Another conventional clinical practice is to suture a catheter hub to a patient's skin to invasively and roughly secure the catheter to the patient. Further still, a variety of catheter and medical tubing securement devices are available for use in the medical field. These securement devices, however, are often bulky and cumbersome, hard to dress and/or remove with a dressing, may require a scissors or scalpel to physically cut them away risking catheter lumen or catheter pigtails damage in the process, may require two, three, or four pieces of tape to get reliable results, and may have costly and complex mechanical features; all of which can combine to both lower patient care clinical outcomes, and equally important, lead to higher healthcare costs due to added nursing costs.

It is also known in the medical field that poorly dressed and poorly secured catheters and associated tubing are likely to undesirably lead to irritation of both internal vascular wall damage at distal catheter tip due to in/out catheter tip motion at the insertion site, necessitating premature rotation and reinsertion of the catheter to a nearby new anatomical insertion site. Even worse, poorly secured catheters are susceptible to accidental dislodgement from the insertion site. For example, medical tubing connected to indwelling catheters, infusion needles and the like is often subjected to inadvertent but significant pulling forces either caused directly by patient movement or by snagging of the tubing on other objects. These pulling forces peel the medical tape or dressing securing the catheter and/or tubing off the patient's skin. This exposes the catheter, infusion needle, etc. to movement inward or outward, increasing the likelihood that the catheter, infusion needle, etc. will fail and have to be replaced and inserted into a new insertion site. Also, this may weaken the adhesion between the dressing and the patient's skin, potentially exposing the insertion site to harmful bacteria.

SUMMARY OF THE INVENTION

The present invention provides a reinforced closure anchor that can close over and anchor a slit, perforation, notch, or edge portion of a medical dressing at which a catheter and/or tubing exits from underneath the dressing. The reinforced closure anchor helps prevent a dressing from inadvertently peeling from a patient's skin, which may be caused by tugging on tubing that is under and exiting from the dressing, by both covering over a portion of the medical dressing and by securing an area of the dressing at which medical tubing exits from underneath the dressing. The reinforced closure anchor also prevents inadvertent peeling by providing additional material beyond the dressing edge, thereby greatly multiplying the dressing withstand in tug force vector directions opposite to (and at any relative angle to, over an entire hemispherical (half globe) field of tug force vectors) that which tubing exits from the dressing. Also, the reinforced closure anchor limits the amount of fabric cloth stretching that can occur by using relatively non-elastic reinforcement material for a spinal structure, which limits the amount and size of a "hole" that can be stretched open by tugs, and thus prevents catheter hubs and/or tubing from "oozing" out of a dressing. And due to the narrow spinal structure's limited portion of entire closure's surface area, higher moisture vapor transmission rate is possible over as much as 90 to 95 percent of the closure's total skin contacting and dressing overlapping surface area.

More particularly, a reinforced closure anchor in accordance with the invention includes a first layer having an adhesive side, an opposite non-adhesive side, and an outer edge. The reinforced closure anchor also includes an anchor member layer having a reinforcing structure, an adhesive member side, and an opposite non-adhesive side. The anchor member adhesive side is adhered to the first layer non-adhesive side. The anchor member may be generally centered between ends of the first layer, the anchor member may extend to portions of the outer edge of the first layer, and the anchor member may have a shape that generally corresponds in shape to a middle portion of the first layer.

The first layer may be a fabric layer, and the reinforced closure anchor may additionally include a film layer having an adhesive skin-adhering side and an opposite side adhered to the first layer adhesive side. Alternatively, the first layer may be a film layer. A release liner may be releasably mounted on the adhesive side of the first (or "bottom") layer.

A reinforced closure anchor in accordance with the invention includes a first layer having an adhesive side, an opposite non-adhesive side, and an outer edge. The reinforced closure anchor also includes an anchor member layer having a reinforcing structure, a top side, and an opposite bottom side. The anchor member top side is adhered to the first layer adhesive side. The anchor member may be generally centered between ends of the first layer, the anchor member may extend to portions of the outer edge of the first layer, and the anchor member may have a shape that generally corresponds in shape to a middle portion of the first layer.

The first layer may be a fabric layer, and the reinforced closure anchor may additionally include a film layer having an adhesive skin-adhering side and an opposite side adhered to the first layer adhesive side. Alternatively, the first layer may be a film layer. A release liner may be releasably mounted on the adhesive side of the first (or "bottom") layer.

These and other features and advantages of the invention will be more fully understood from the following detailed description of the invention taken together with the accompanying drawings.

BRIEF DESCRIPTION OF THE DRAWINGS

In the drawings:

FIG. 1 is a plan view of a reinforced closure anchor in accordance with the invention;

FIG. 3 is a cross-sectional view of the reinforced closure anchor taken along the line 3-3 in FIG. 1;

FIG. 4 is an environmental view of the reinforced closure anchor of FIG. 1 securing and stabilizing a dressing;

FIG. 5 is a plan view of a reinforced closure anchor in accordance with the invention;

FIG. 7 is a cross-sectional view of the reinforced closure anchor taken along the line 7-7 in FIG. 5;

FIG. 11 is a plan view of a reinforced closure anchor in accordance with the invention;

FIG. 13 is a cross-sectional view of the reinforced closure anchor taken along the line 13-13 in FIG. 11.

DETAILED DESCRIPTION OF THE INVENTION

Figure 2:
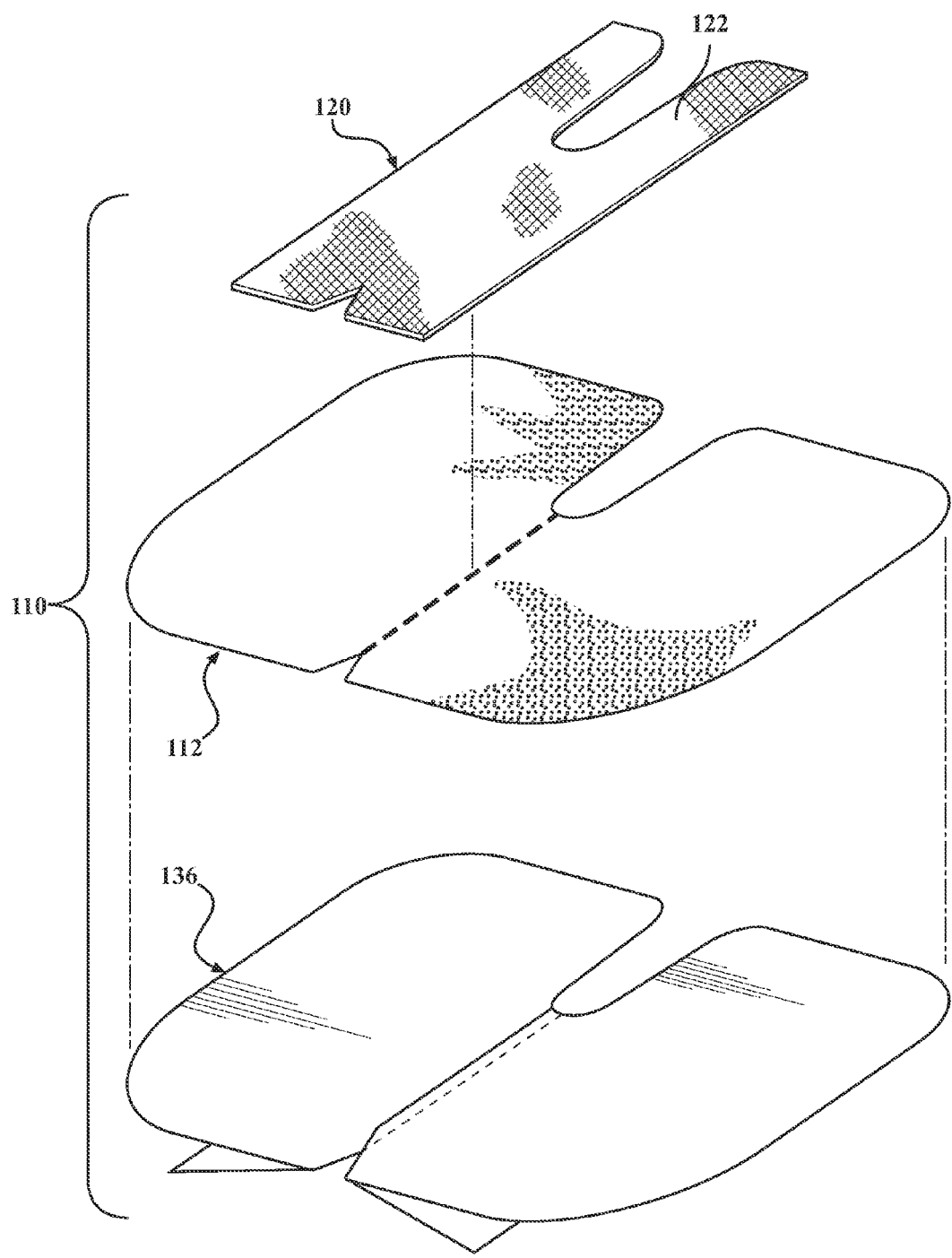
FIG. 2 is an exploded view of the reinforced closure anchor of FIG. 1.

Referring now to the drawings in detail, numeral 110 generally indicates a reinforced closure anchor in accordance with the invention. The reinforced closure anchor 110 may secure a portion of a medical dressing, such as a portion at which medical tubing exits from underneath the dressing. The reinforced closure anchor 110 counteracts tugging forces from any hemispherical vector direction that may be applied on the medical tubing and helps prevent the tugging forces from pulling the dressing away from a patient's skin.

Turning to FIGS. 1 through 3, the reinforced closure anchor 110 includes a first layer 112 having an adhesive side 114 including an adhesive such as a medical skin contact grade adhesive or similarly suitable adhesive thereon. The first layer 112 also has an opposite non-adhesive side 116 and an outer edge 118. The first layer 112 is not limited to any particular shape. In the embodiment shown in the drawings, the first layer 112 is generally rectangular in shape with curved corners. The first layer 112 may be made of a woven or non-woven fabric material. Alternatively, the first layer 112 may be made of a film such as a polyurethane film or similar.

An anchor member layer 120 including a reinforcing structure 122 is disposed on a "top" side of the first layer 112. The anchor member 120 may be made of a polypropylene or polyethylene net or net-like material or another similar material, such as woven or non-woven or cellulosic or foam or other laminar materials having sufficient non-elastic properties yet being flexible, "contourable" and permeable, and having rigidizing and force spreading properties as discussed below, wherein the netting defines the reinforcing structure 122. The anchor member 120 has an adhesive side 124 including a suitable adhesive thereon. The anchor member 120 also has an opposite non-adhesive side 126. The anchor member adhesive side 124 is adhered to the first layer non-adhesive side 116.

The anchor member 120 is not limited to any particular shape, although the anchor member typically has less surface area than the first layer such that the anchor member only overlaps a portion of the first layer. For example, the anchor member 120 may have approximately half or less than half the surface area of the first layer 112. The anchor member 120 is generally centered between ends of the first layer 112, and the anchor member has a shape that generally corresponds in shape to a middle portion of the first layer. For example, the anchor member 120 may extend to portions of the outer edge 118 of the first layer 112 and may have a shape that corresponds to an entire middle ⅓ portion of the first layer.

The anchor member 120 strengthens the reinforced closure anchor 110 by making it less floppy for easier application. More importantly, as shown in FIG. 4, when the reinforced closure anchor 110 is applied over a portion of a dressing 150 and under the exiting tubing 152 (as well as to a patient's skin 154 where it is not over the dressing), the anchor member 120 spreads the localized external tubing tug forces that are exerted on the dressing 150 and the reinforced closure anchor 110 over a large surface area, greatly increasing the dressing's resistance to premature separation from the patient's skin by not permitting the dressing to elongate and break the adhesive forces between the dressing and the patient's skin. Likewise, the anchor member 120 increases the amount of force necessary to separate the dressing 150, and thus the catheter 156, from a patient's skin 154. With the use of the reinforced closure anchor 110, external forces exerted on a dressing are not as localized. Highly concentrated localized tug forces are a typical reason small forces are able to commence peeling of a dressing by stretching the fabric and film of the dressing in a local area which then propagates onward. Commonly, forces external to the dressing are exerted on a dressing by pulling, snagging, or tugging on the IV connector ports, IV valves, pigtails, lumen, fittings, and/or medical fluid administration tubing that are connected to a catheter underneath the dressing. For example, movement of the medical tubing may be caused by the patient moving, by snagging of the tubing on other neighboring objects, by a clinician moving the tubing or the patient, or any combination of the above. The reinforced closure anchor 110 also prevents premature separation of a dressing from a patient's skin by preventing the dressing from stretching and thus peeling when the dressing is tugged on as described above, for example, when the tubing connected to the catheter hub is pulled. Stretching of a dressing locally (and resultant peel propagation) can ultimately lead to a dressing separating fully from a patient's skin. In sum, the reinforced closure anchor 110 greatly increases the withstand of a dressing and greatly increases the amount of any hemispherical vector multi-directional pulling force that is necessary to cause a dressing to separate from a patient's skin. This leads directly to longer dwell times, better patient care, lower nursing time, and lower healthcare costs.

The reinforced closure anchor 110 may be generally symmetrical about one of its axes 128. A closure perforation line 130, for easy removal of the closure anchor and associated dressing, may extend across the first layer 112 and the anchor member 120. In other words, the reinforced closure anchor 110 is perforated through all of layers (not including any release liner layer(s)—see below) along the perforation line 130. The perforation line 130 may extend along the axis of symmetry 128, thereby dividing the reinforced closure anchor 110 into two mirror image portions and allowing the reinforced closure anchor to be separated at a dressing removal time while the closure anchor is still overlapped onto the dressing on either side of the tubing. A V-shaped notch 132 may be disposed along the first layer outer edge 118 at an end of the perforation line 130. The V-shaped notch 132 serves as a landmark indicating where the perforation line 130 is located. A deep U-shaped recess 134 is disposed along the first layer outer edge 118. The U-shaped recess 134 may be at an opposite end of the perforation line 130 relative to the V-shaped notch 132. When the reinforced closure member 110 is applied to a dressing in an area where medical tubing exits from underneath the dressing, closure anchor's U-shaped recess 134 is slid under the tubing and overlapped on top of the dressing behind the catheter hub, creating opposing U-slot "keyholes" that the catheter hub cannot be easily tugged out of. The U-slot "keyholes" and the added surface area beyond the dressing's edge strengthen the dressing and greatly increase the magnitude of a tug force necessary to raise the dressing's edge from a patient's skin, thereby improving securement and stabilization. The U-shaped recess 134 also makes it easier to create an occlusive barrier at the tubing exit point.

The reinforced closure anchor 110 may further include a release liner 136 releasably mounted on the adhesive side 114 of the first layer 112. The release liner 136 may include a first member 138 and a second member 140. The first member 138 includes a first portion 142 and a second portion 144 and the second member 140 includes a first portion 146 and a second portion 148. The first portions 142, 146 are mounted on the first layer adhesive side 114 and the second portions 144, 148 are folded relative to the first portions to form gripping tabs. The first member 138 may overlap the second member 140, and each of the first and second members may be released from the first layer adhesive side 114 without tampering with the other of the members.

To apply the reinforced closure anchor 110, preferably only one of the first and second members 138, 140 of the release liner 136 is removed to expose part of the first layer adhesive side 114. For example, the first member 138 may be removed by gripping the gripping tab 144 and pulling the first member 138 away from the fabric layer adhesive side 114. By leaving the second member 140 of the release liner 136 in place, a user may grasp part of the reinforced closure anchor 110 without the user's fingers becoming stuck to the reinforced closure anchor. Next, the reinforced closure anchor 110 is positioned where it is desired to apply the reinforced closure anchor 110. For example, the reinforced closure anchor 110 may be applied to an edge portion of a dressing at which tubing exits from underneath the dressing. The reinforced closure anchor 110 is positioned so that the closure anchor is under the tubing with the U-shaped recess 134 laying on either side of the tubing and overlapping the top surface of the dressing. The exposed first layer adhesive side 114 is then adhered to the outside of the dressing and any portion of the patient's skin that is exposed underneath the reinforced closure anchor. Next, the second member 140 of the release liner 136 is removed by pulling the gripping tab 148, and the rest of the reinforced closure anchor 110 is applied to the dressing and/or patient's skin.

Alternatively, the reinforced closure anchor 110 may be used in lieu of tape strips to secure medical tubing, such as IV tubing, to a patient's skin.

To remove the closure anchor 110 and dressing from a patient's skin, the closure anchor is separated along the perforation line 130 by tearing the perforation line. The closure anchor 110 and dressing may then be removed from the patient's skin as a single unit by pulling the closure anchor 110 and dressing away from the tubing and catheter hub, making it safer and easier to remove the dressing from the tubing and hub with a lowered risk of unwanted catheter movement.

Figure 6:
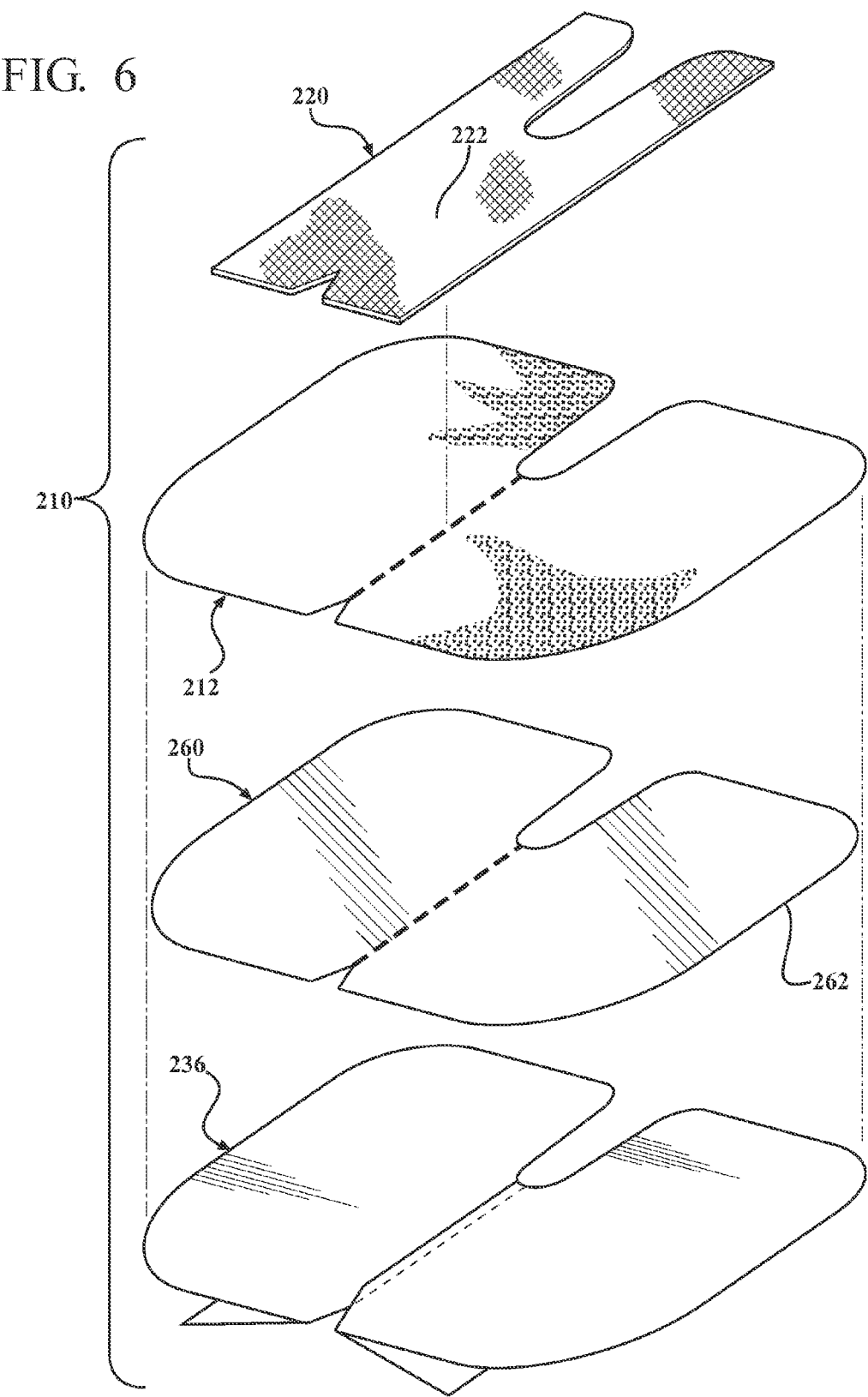
FIG. 6 is an exploded view of the reinforced closure anchor of FIG. 5.
Figure 8:
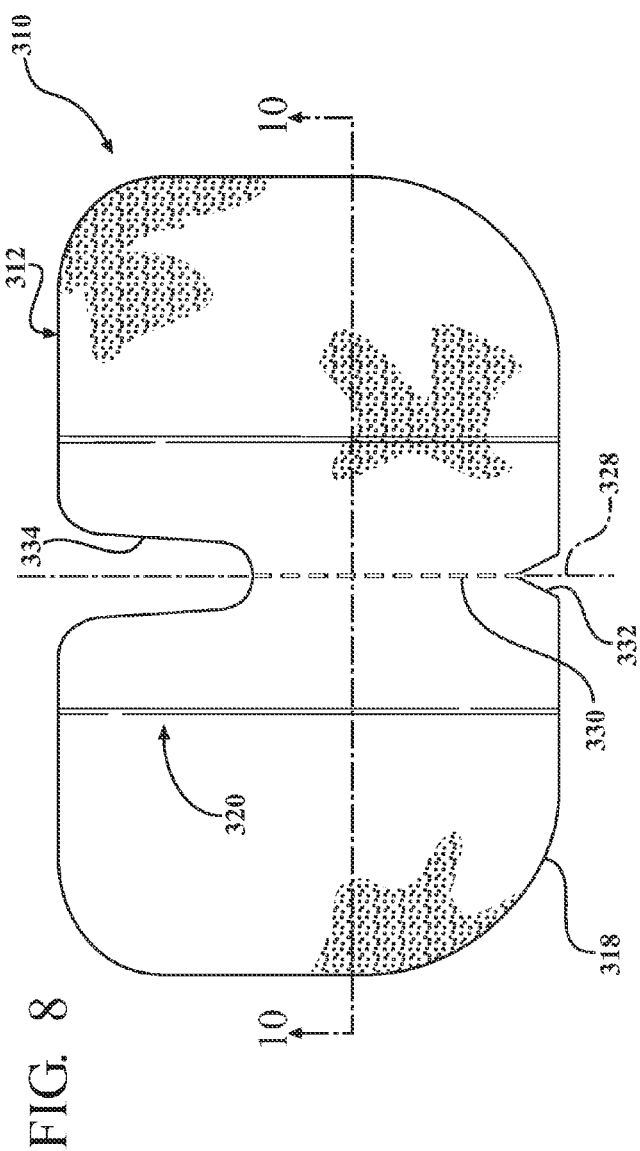
FIG. 8 is a plan view of a reinforced closure anchor in accordance with the invention.
Figure 10:
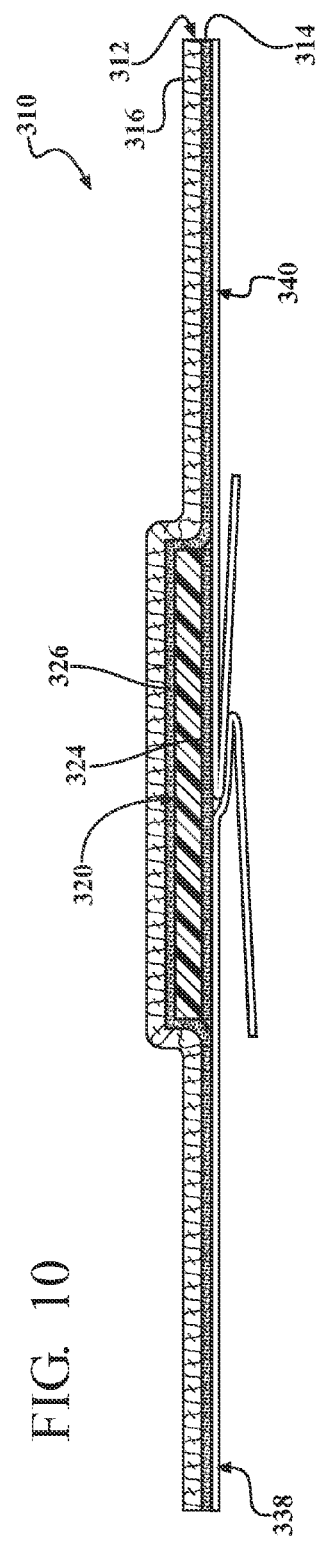
FIG. 10 is a cross-sectional view of the reinforced closure anchor taken along the line 10-10 in FIG. 8.
Figure 9:
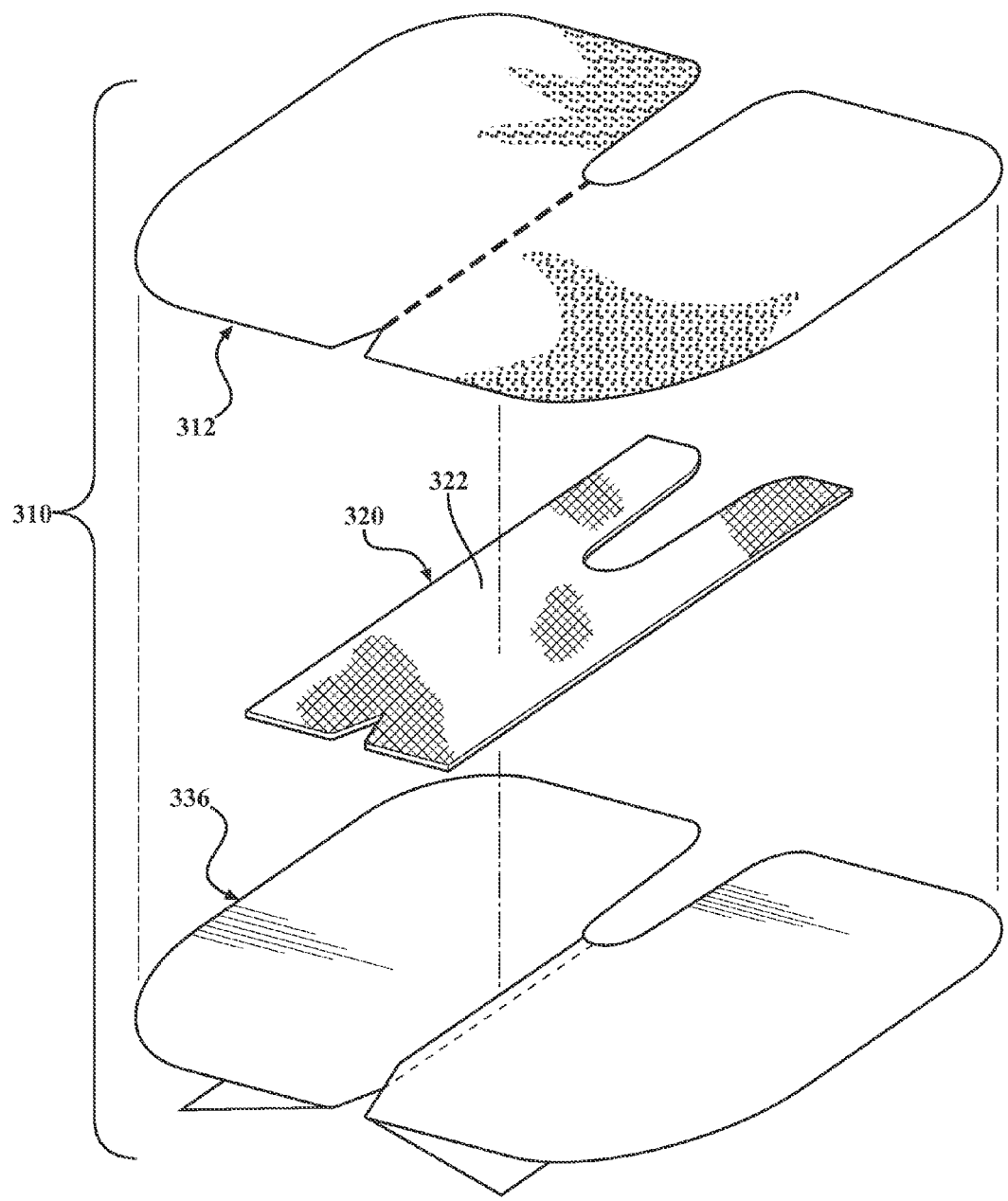
FIG. 9 is an exploded view of the reinforced closure anchor of FIG. 8.

In another embodiment, the reinforced closure anchor may further include both a fabric layer such as a woven or non-woven fabric or similar, and a film layer such as a polyurethane film or similar. As shown in FIGS. 5-7, the reinforced closure anchor 210 includes a fabric layer 212 and an anchor member layer 220 including a reinforcing structure 222 disposed on and adhered to a "top" non-adhesive side 216 of the fabric layer 212. The fabric layer 212 and anchor member layer 220 may have any of the features described in the previous embodiments. The reinforced closure anchor 210 further includes a film layer 260 having an adhesive skin-adhering side 262. The adhesive on the skin-adhering side 262 may be a medical skin contact grade adhesive or similarly suitable adhesive. A side of the film layer 260 opposite the skin-adhering side 262 is disposed adjacent the fabric layer 212 and is adhered to the fabric layer. A release liner 236 may be releasably mounted on the skin-adhering side 262 of the film layer 260. The film layer 260 may have a shape that is coincident with the fabric layer 212 and/or film layer 260. The film layer 260 may make the reinforced closure anchor 210 more comfortable for a patient by shielding the fabric layer 212 from the patient's skin. The film layer 260 also can create a bacterial barrier and can add stack strength to the closure anchor.

In this embodiment of the reinforced closure anchor 210, the anchor member layer 220 has the same size and shape as the anchor member layer in the first embodiment 110.

In yet another embodiment shown in FIGS. 8-11, the reinforced closure anchor 310 includes a first layer 312 having an adhesive side 314 including an adhesive such as a medical skin contact grade adhesive or similarly suitable adhesive thereon. The first layer 312 also has an opposite non-adhesive side 316 and an outer edge 318. The first layer 312 is not limited to any particular shape. In the embodiment shown in the drawings, the first layer 312 is generally rectangular in shape with curved corners. The first layer 312 may be made of a woven or non-woven fabric material. Alternatively, the first layer 312 may be made of a film such as a polyurethane film or similar.

An anchor member layer 320 including a reinforcing structure 322 is disposed on a "bottom" side of the first layer 312. The anchor member 320 may be made of a polypropylene or polyethylene net or net-like material or another similar material, such as woven or non-woven or cellulosic or foam or other laminar materials having sufficient non-elastic properties yet being flexible, "contourable" and permeable, and having rigidizing and force spreading properties as discussed below, wherein the netting defines the reinforcing structure 322. The anchor member 320 has a first side 324 that is a "bottom" side and an opposite second side 326 that is a "top" side. The anchor member first side 324 may include a suitable adhesive thereon. The anchor member 320 is disposed within the outer edge 318 of the first layer 312. In contrast to the first embodiment 110, the anchor member "top" second side 326 is adhered to the first layer adhesive "bottom" side 314. Otherwise, the reinforced closure anchor 310 has similar features and functions as the first embodiment 110.

For example, the reinforced closure anchor 310 may be generally symmetrical about one of its axes 328. A closure perforation line 330, for easy removal of the closure anchor and associated dressing, may extend across the film layer 312 and the anchor member 320. In other words, the reinforced closure anchor 310 is perforated through all of layers (not including any release liner layer(s)) along the perforation line 330. The perforation line 330 may extend along the axis of symmetry 328, thereby dividing the reinforced closure anchor 310 into two mirror image portions and allowing the reinforced closure anchor to be separated at a dressing removal time while the closure anchor is still overlapped onto the dressing on either side of the tubing. A V-shaped notch 332 may be disposed along the film layer outer edge 318 at an end of the perforation line 330. The V-shaped notch 332 serves as a landmark indicating where the perforation line 330 is located. A deep U-shaped recess 334 is disposed along the film layer outer edge 318. The U-shaped recess 334 may be at an opposite end of the perforation line 330 relative to the V-shaped notch 332. A release liner 336 may be releasably mounted on the adhesive side 314 of the first layer 312. The release liner may have first and second members 338, 340.

The anchor member 320 is not limited to any particular shape, although the anchor member typically has less surface area than the first layer such that the anchor member only overlaps a portion of the first layer. For example, the anchor member 320 may have approximately half or less than half the surface area of the first layer 312. The anchor member 320 is generally centered between ends of the first layer 312, and the anchor member has a shape that generally corresponds in shape to a middle portion of the first layer. For example, the anchor member 320 may extend to portions of the outer edge 318 of the first layer 312 and may have a shape that corresponds to an entire middle ⅓ portion of the first layer.

Figure 12:
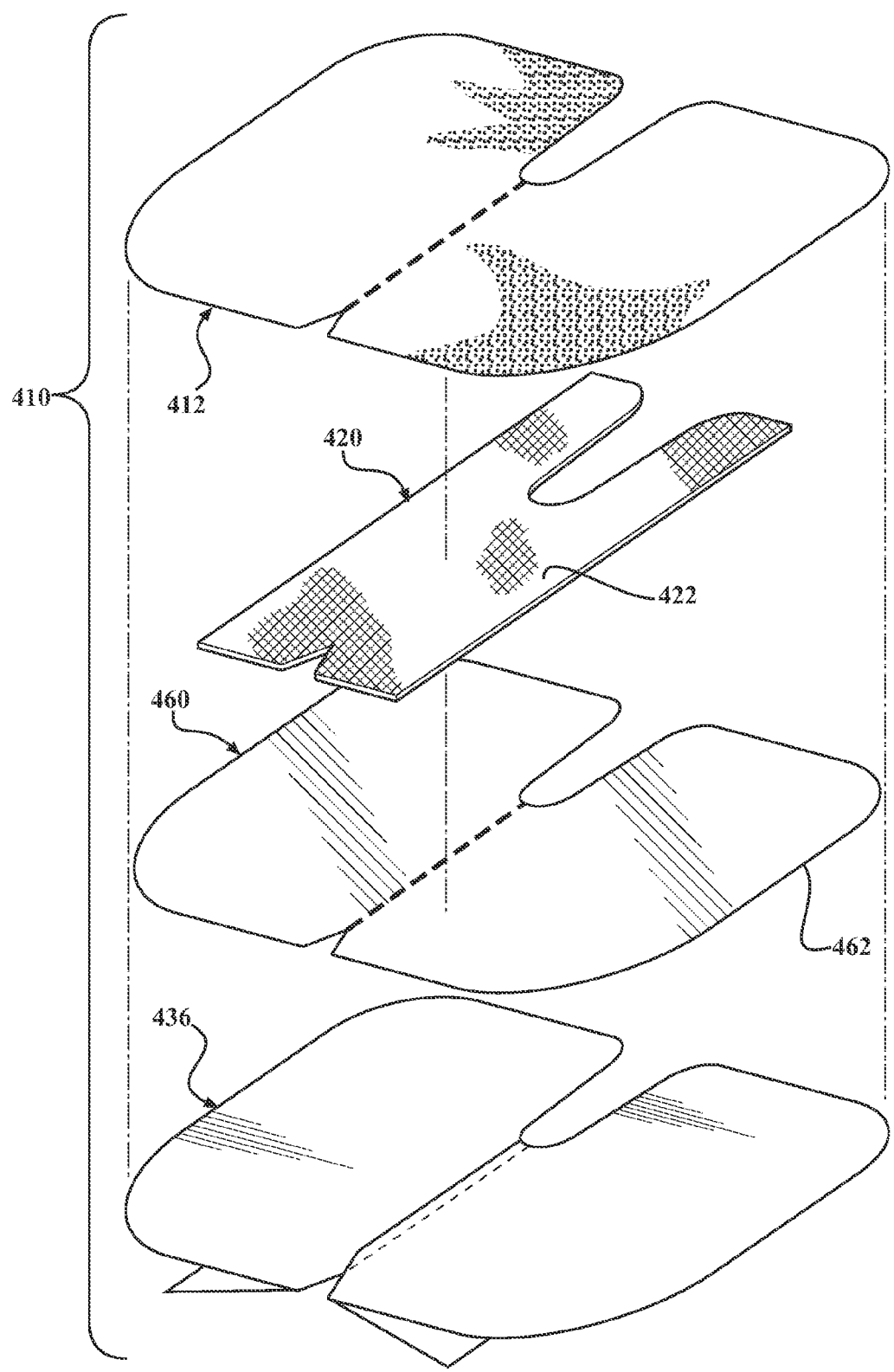
FIG. 12 is an exploded view of the reinforced closure anchor of FIG. 11.

In another embodiment, the reinforced closure anchor may further include both a fabric layer such as a woven or non-woven fabric or similar, and a film layer such as a polyurethane film or similar. As shown in FIGS. 11-13, the reinforced closure anchor 410 includes a fabric layer 412 and an anchor member layer 420 including a reinforcing structure 422 disposed on and adhered to a "bottom" adhesive side 414 of the fabric layer 412. The fabric layer 412 and anchor member layer 420 may have any of the features described in the previous embodiments. The reinforced closure anchor 410 further includes a film layer 460 having an adhesive skin-adhering side 462. The adhesive on the skin-adhering side 462 may be a medical skin contact grade adhesive or similarly suitable adhesive. A side of the film layer 460 opposite the skin-adhering side 462 is disposed adjacent the fabric layer 412 and is adhered to the fabric layer. A release liner 436 having first and second members 438, 440 may be releasably mounted on the skin-adhering side 462 of the film layer 460. The film layer 460 may have a shape that is coincident with the fabric layer 412 and/or film layer 460. The film layer 460 may make the reinforced closure anchor 410 more comfortable for a patient by shielding the fabric layer 412 and the anchor member layer 420 from the patient's skin. The film layer 460 also can create a bacterial barrier and can add stack strength to the closure anchor.

In this embodiment of the reinforced closure anchor 410, the anchor member layer 420 has the same size and shape as the anchor member layer in the third embodiment 310.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A reinforced closure anchor comprising:
   a first layer having an adhesive side, an opposite non-adhesive side, and an outer edge; and
   an anchor member layer having a reinforcing structure, an adhesive side, and an opposite non-adhesive side, said anchor member adhesive side being adhered to said first layer non-adhesive side;
   said anchor member being generally centered between ends of said first layer, said anchor member extending to portions of said outer edge of said first layer, and said anchor member having a shape that generally corresponds in shape to a middle portion of said first layer.

2. The reinforced closure anchor of claim 1, wherein said first layer is a fabric layer.

3. The reinforced closure anchor of claim 2, including a film layer having an adhesive skin-adhering side and an opposite side adhered to said fabric layer adhesive side.

4. The reinforced closure anchor of claim 1, wherein said first layer is a film layer.

5. The reinforced closure anchor of claim 1, including a release liner releasably mounted on the adhesive side of said first layer.

6. The reinforced closure anchor of claim 3, including a release liner releasably mounted on the adhesive side of said film layer.

7. A reinforced closure anchor comprising:
   a first layer having an adhesive side, an opposite non-adhesive side, and an outer edge; and
   an anchor member layer having a reinforcing structure, a top side, and an opposite bottom side, said anchor member top side being adhered to said first layer adhesive side;
   said anchor member being generally centered between ends of said first layer, said anchor member extending to portions of said outer edge of said first layer, and said anchor member having a shape that generally corresponds in shape to a middle portion of said first layer.

8. The reinforced closure anchor of claim 7, wherein said first layer is a fabric layer.

9. The reinforced closure anchor of claim 8, including a film layer having an adhesive skin-adhering side and an opposite side adhered to said fabric layer adhesive side.

10. The reinforced closure anchor of claim 7, wherein said first layer is a film layer.

11. The reinforced closure anchor of claim 7, including a release liner releasably mounted on the adhesive side of said first layer.

12. The reinforced closure anchor of claim 10, including a release liner releasably mounted on the adhesive side of said film layer.

* * * * *